United States Patent
Van Breugel et al.

(10) Patent No.: US 6,630,603 B1
(45) Date of Patent: Oct. 7, 2003

(54) METHOD OF INDUSTRIAL-SCALE PURIFICATION OF LACTIC ACID

(75) Inventors: Jan Van Breugel, Woudrichem (NL); Jan Van Krieken, Gorinchem (NL); Agusti Cerda Baró, Cerdanyola Del Valles (ES); José Maria Vidal Lancis, Vilassar De Mar (ES); Margarita Camprubi Vila, Sabadell (ES)

(73) Assignee: Purac Biochem B.V., Gorinchem (NL)

( * ) Notice: Subject to any disclaimer, the term of this patent is extended or adjusted under 35 U.S.C. 154(b) by 0 days.

(21) Appl. No.: 09/937,219

(22) PCT Filed: Mar. 21, 2000

(86) PCT No.: PCT/NL00/00189

§ 371 (c)(1),
(2), (4) Date: Jan. 16, 2002

(87) PCT Pub. No.: WO00/56693

PCT Pub. Date: Sep. 28, 2000

(30) Foreign Application Priority Data

Mar. 22, 1999 (NL) .............................................. 1011624

(51) Int. Cl.$^7$ .............................................. C07C 51/42
(52) U.S. Cl. ...................................... 562/580; 562/589
(58) Field of Search .................................. 562/580, 589

(56) References Cited

PUBLICATIONS

Borsook, H et al Journal of Biological Chemistry vol. 102, 1933 p. 449–460.*

* cited by examiner

*Primary Examiner*—Paul J. Killos
(74) *Attorney, Agent, or Firm*—Sughrue Mion, PLLC

(57) ABSTRACT

The present invention relates to a method of industrial-scale purification of lactic acid, the method including the steps of:
 (a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1; and
 (b) subjecting the concentrated lactic acid solution to a crystallization to form a pure lactic acid.

The invention also relates to the lactic acid or the lactic acid solution obtained via this method, and the use thereof.

23 Claims, No Drawings

METHOD OF INDUSTRIAL-SCALE PURIFICATION OF LACTIC ACID

This application is a 371 of PCT/NL00/00189 Mar. 21, 2000.

The present invention relates to a method of industrial-scale purification of lactic acid and to chirally extremely pure products which can be obtained via this method and to uses thereof.

Lactic acid is generally sold as a dilute or concentrated solution, since lactic acid has a strong tendency to form intermolecular esters (dimeric and polymeric lactic acid). Furthermore, lactic acid (even highly pure lactic acid) is strongly hygroscopic. Industrial-scale purification of lactic acid (the racemic mixture and in particular the enantiomers of lactic acid) is a complicated and laborious process according to the prior art.

It is known to prepare lactic acid, or 2-hydroxypropionic acid, by way of fermentation. In general, the fermentative preparation of lactic acid first of all comprises a fermentation step in which a carbohydrate-containing substrate such as glucose or sucrose is converted to lactic acid by a suitable microorganism. Known microorganisms producing (S)-lactic acid are various bacteria of the genus Lactobacillus. for example Lactobacillus casei. Also known, apart from these, are microorganisms which selectively produce (R)-lactic acid. The aqueous fermentation product is then worked up so that lactic acid is obtained. The customary industrial work-up route generally consists of the removal of the biomass, followed by acidification, purification and concentration.

In the case of (S)-lactic acid, the lactic acid thus obtained is sufficiently pure for incorporation into comestibles for human consumption. (S)- or (R)-lactic acid which is ultimately obtained by means of this customary method can have an enantiomeric purity of 98% or even higher (i.e. at 98% or more of the lactic acid present consists of the (S)- or (R)-enantiomer). However, the product still contains residual sugars and other impurities. Moreover, the product has a yellow colour and, when heated, turns brown or even black, due to decomposition of impurities. Furthermore, the product has an unpleasant odour. In addition. in the case of (S)-lactic acid the organoleptic properties are often unsatisfactory. The lactic acid enantiomer is therefore moderately suitable for use in foods, but entirely unsuitable for pharmaceutical applications and in syntheses of chiral compounds.

By means of esterification followed by hydrolysis, the purity of the product can be increased, so that it is suitable for pharmaceutical applications. As a result of this esterification/hydrolysis the enantiomeric purity decreases, however, and the lactic acid still contains a small amount of the alcohol used in the esterification. Examples of other methods of purifying lactic acid comprise subjecting aqueous solutions of lactic acid to one or more extraction, (steam) distillation and/or evaporation steps, electrodialysis steps and crystallizations (see e.g. Ullmans Encyklopädie der Technischen Chemie, Verlag Chemie GmbH, Weinheim, Fourth Edition, Volume 17. pp. 1–7 (1979); H. Benninnga "History of Lactic Acid Making", Kluwer Academic Publishers, Dordrecht-Boston-London (1990); C. H. Holten, "Lactic Acid; Properties and Chemistry of Lactic Acid and Derivatives", Verlag Chemie GmbH, Weinheim (1971); The Merck Index, Merck & Co., Inc., eleventh edition, p. 842 (1989); Römmp Chemie Lexicon, G. Thieme Verlag, Stuttgart and New York, Ninth Edition, Volume 4, pp. 2792–2893 (1991) and the Dutch Patent Applications 1013265 and 1013682.

The German Patent 593,657 (granted on Feb. 15, 1934) describes a laboratory experiment in which an aqueous solution of lactic acid which contained an excess of the (S)-component and virtually no lactic anhydride was concentrated by means of a thin-film evaporation technique, at reduced pressure if required, the lactic acid being separated in the process from impurities having a boiling point lower than that of lactic acid. Then the concentrated lactic acid solution was rapidly cooled to form crystals. The crystals were then separated from the mother liquor, washed with ether and recrystallized a sufficient number of times from ethyl acetate or chloroform or a comparable solvent for the crystals to exhibit a sharp melting point of 53° C. The total lactic acid content, the content of monomeric lactic acid, the chiral purity or the enantiomeric excess and the colour are not reported. Moreover, it is obvious to those averagely skilled in the art that such a method is not suitable for efficient industrial-scale purification, especially given the use of solvents such as ether, ethyl acetate or chloroform, which are flammable and/or toxic solvents whose use on an industrial scale is currently not permitted or is subject to very strict standards.

H. Borsook, H. M. Huffman, Y-P. Liu, J. Biol. Chem. 102, 449–460 (1933) describes a laboratory experiment in which an aqueous mixture which contained 50% lactic acid with an excess of (S)-lactic acid, 30% lactic anhydride and lactic acid dimer and 15% water, were subjected to fractional distillation at about 0.13 mbar and 105° C. The middle fraction was subsequently redistilled and then cooled in an ice/salt bath to form a solid mass of crystals. It is stated that the distillation must be carried out using small amounts, as larger amounts will result in a substantial loss of product, owing to the long heating time. The solid mass of crystals was then recrystallized three times from an equal volume of equal quantities of diethyl ether and diisopropyl ether. the crystals were isolated and dried at room temperature in a vacuum desiccator. Thus it was possible to obtain (S)-lactic acid having a melting point of 52.7–52.8° C., which contained less than 0.1% of impurities such as water, lactic anhydride or lactic acid dimer. Again, the chiral purity and the colour are not stated here. Moreover, it is obvious to those averagely skilled in the art that this method too is not suitable for efficient industrial-scale purification.

L. B. Lockwood, D. E. Yoder, M. Zienty, Ann. N.Y. Acad. Sci. 119, 854 (1965) likewise describe distillation and crystallization of lactic acid on a laboratory scale, where the melting point of the optically pure lactic acid obtained was 54° C. The colour and other important properties are not reported.

In 1934, Boehringer Ingelheim studied the crystallization of lactic acid, but this method was found not to produce good results, owing to problems with purification and further treatment. After the Second World War, however, Boehringer Ingelheim proved able to produce lactic acid for pharmaceutical applications on a scale of about 12 to 15 tonnes per month with a yield of about 77 to 86%. This involved purification of an aqueous solution of lactic acid by means of steam distillation at reduced pressure (about 13 mbar) followed by crystallization at −25° C., the crystals then being dissolved in water and the solution being treated with potassium ferrocyanide (to remove heavy metals) and activated carbon. The chiral purity or other properties such as colour and odour of the (S)-lactic acid thus produced are not known. U.S. Pat. No. 5,64,406 discloses a process for the production and purification of lactic acid by ion exchange. In column, line 67—column 2, line , it is further disclosed that cation-free lactic acid solutions can be evaporated or crystallized.

Crystalline (S)-lactic acid has been launched onto the market at purities of more than 99% by Fluka and Sigma, for example, (see, for example, M. L. Buszko, E. R. Andrew, Mol. Phys. 76, 83–87 (1992) and T. S. Ing, A. W. Yu, V. Nagaraja, N. A. Amin, S. Ayache, V. C. Gandhi, J. T. Daugirdas, Int. J. Artif. Organs 17, 70–73 (1994)). Crystalline (S)-lactic acid having a water content of less than 1% by weight is known from Example 1 of EP-A-563,455. The crystal structure of lactic acid is described in A. Schouten, J. A. Kanters, J. van Krieken, J. Mol. Struct. 323, 165–168 (1994).

Lactic acid can also be obtained synthetically. This is known. The product of the synthetic preparation approach, however, is a racemic mixture which therefore contains (S)-lactic acid and (R)-lactic acid in equal amounts. Whilst the individual enantiomers can be separated by means of known techniques, such as diastereoisomer separation techniques, one of the enantiomers crystallizing out as a salt and said salt then being reconverted into the enantiomeric lactic acid, the enantiomeric product ultimately obtained will inevitably still contain significant quantities of the other enantiomer.

It has been found that, using the prior art methods, industrial-scale production of lactic acid having a high chiral and a high chemical purity and, especially for pharmaceutical applications, an acceptable colour and odour is not possible.

The invention therefore relates to a method of industrial-scale (i.e. a production capacity of at least 1000 tonnes per annum) purification of lactic acid, the method comprising the steps of:

(a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1, to form a lactic acid concentrate, and (b) subjecting the lactic acid concentrate to a crystallization to form a pure lactic acid.

The total acid content (TA) is the acid content after saponification of intermolecular ester bonds with an excess of base and is determined by back titration with acid. The total acid content therefore represents the amount of monomeric, dimeric and polymeric lactic acid. The free-acid content (FA) is determined by direct titration with base, i.e. prior to saponification of the intermolecular ester groups. The monomeric lactic acid content (ML) is defined here as:

$$ML = TA - 2 \times (TA - FA)$$

provided that TA−FA<10%. This means that not very much dimeric or polymeric lactic acid must be present. Moreover, it is assumed that the non-monomeric lactic acid is present in the form of lactoyl lactic acid (dimer).

Chiral purity (for an excess of (S)-isomer) is defined here as:

$$\text{Chiral purity} = 100\% \times \{[(S)\text{-isomer}]/[(R)\text{-isomer} + (S)\text{-isomer}]\}$$

A further object of the invention is to provide a method which is economically attractive and technically feasible and which, in the case of (S)-lactic acid, also affords a product having excellent organoleptic properties.

Using the method according to the invention it is possible to obtain a lactic acid product which is both colourless and chirally pure. The degree of coloration is determined in accordance with ASTM D 5386-93 and is expressed in "APHA units". The method is suitable for determining the coloration of clear liquids. A coloration of at most 10 APHA units means that the liquid in question has a visually imperceptible coloration and, as perceived with the naked eye, is therefore colourless. The coloration after heating (for about two hours under reflux) is preferably at most 20 APHA units.

According to the invention it is preferable for the concentrated lactic acid solution to be distilled under reduced pressure to form a lactic acid concentrate having a total acid content of at least 98 wt %, preferably at least 99 wt %, the lactic acid concentrate containing at least 95 wt % monomeric acid, based on the lactic acid concentrate, and a distillation residue. Preferably, the lactic acid concentrate contains at least 98.5 wt % of monomeric lactic acid. The chiral purity of the lactic acid concentrate is preferably 90% or more, more preferably 95% or more, and in particular 99% or more. Within the scope of the invention, reduced pressure is to be understood as a pressure in the range of from 0.1 to 20 mbar, in particular from 0.2 to 10 mbar. The temperature during the distillation under reduced pressure is preferably from 100 to 200° C., in particular from 110 to 140° C. The distillation under reduced pressure results in the removal of impurities having a high boiling point, as the lactic acid is obtained as the top product. According to the invention, this distillation under reduced pressure is carried out, in particular, with the aid of a short-path distillation apparatus. The distillation under reduced pressure can also be carried out at a pressure of from 0.1 to 20 mbar, in particular from 2 to 10 mbar, and at a temperature of from 100° to 200° C., in particular a temperature of from 110° to 140° C., the concentrated lactic acid solution preferably being brought into the vapour phase by means of film evaporation, the vapour then being passed to a distillation column. In the process, separation into two fractions occurs under reflux, the top product containing at least 98 wt % of total acid, preferably at least 99 wt %, and the residue containing residual sugars and polymeric lactic acid. The top product contains at least 95 wt % of monomeric lactic acid, based on the lactic acid concentrate. Preferably, the top product contains at least 99.5 wt % of monomeric lactic acid. The chiral purity of this top product is preferably 90% or more, more preferably 95% or more, and in particular 99% or more. According to this preferred embodiment, the film evaporation preferably takes place by means of lubricated film evaporation, thin-film evaporation and/or falling-film evaporation, the distillation column or columns having a number of trays of from 1 to 10. Distillation step (a) ensures that lactic acid is separated from components such as residual sugars and polymeric lactic acid and components which impart a colour to the impure lactic acid. These components or impurities have a boiling point which is higher than that of lactic acid.

According to the invention, the concentrated lactic acid solution, prior to distillation step (a), can be passed over a column containing activated carbon and/or over an ion exchanger, preferably first over the column(s) containing activated carbon and then over the ion exchanger(s).

The invention further relates to lactic acid or a lactic acid solution having a total acid content of at least 99 wt %, a monomer content of at least 99 wt %, a chiral purity of at least 99% and a colour of at most 10 APHA units, the lactic acid or the lactic acid solution having an acceptable odour, in particular for pharmaceutical applications. In the case of a lactic acid solution the solvent is preferably water, although other solvents such as $C_1$–$C_5$ alkanols (methanol, ethanol, 1-propanol, 2-propanol, 1-butanol, 2-butanol, 2-methyl-1-propanol, 2-methyl-2-propanol, 1-pentanol, 2-pentanol, 3-pentanol, 2-methyl-1-butanol, 2-methyl-2-butanol, 3-methyl-1-butanol, 3-methyl-2-butanol and 2,2-dimethylpropanol) are also suitable. The chiral purity is at least 99%, in particular at least 99.5%, which corresponds to 99% enantiomeric excess ("ee") or higher. The greatest preference is given to lactic acid or the solution thereof whose chiral purity is at least 99.8% (i.e. at least 99.6% ee). The lactic acid or the lactic acid solution further satisfies the following characteristics:

alcohol content: not more than 250 ppm (alcohol is methanol, ethanol or some other alcohol, as the alcohol as such or in the form of a lactate), total nitrogen: not more than 5 ppm, total sugar: not more than 100 ppm, organic acids (other than lactic acid): not more than 250 ppm.

The lactic acid or the lactic acid solution represents, in terms of odour, a marked improvement for use in foods and a higher chemical purity than the products according to the prior art.

The lactic acid according to the invention can be both (S)-lactic acid and (R)-lactic acid, depending on the microorganism used in the fermentation.

Both the (S)-lactic acid and the (R)-lactic acid or their solutions can very suitably be used, because of their high chiral purity, for chiral syntheses. The chirally pure (S)-lactic acid or solutions thereof are highly suitable, furthermore, for use in pharmaceutical preparations. The chirally pure lactic acid is particularly suitable, furthermore, for the production of poly(lactic acid) and/or copolymers with poly(lactic acid).

The invention therefore also relates to a pharmaceutical preparation comprising the above-described (S)-lactic acid or the (S)-lactic acid solution.

Preparation of the Concentrated Lactic Acid Solution

According to the invention, the concentrated lactic acid solution which is subjected to the distillation under reduced pressure is prepared from a feed which, in principle, can be any lactic-acid-containing stream having a total acid content of at least 80 wt %, preferably at least 90 wt %, based on the feed stream in total. The content of monomeric lactic acid of the feed is likewise at least 80 wt % and preferably at least 90 wt %. At the same time, the ratio between the two lactic acid enantiomers in the feed must not be equal to 1, which means that the lactic-acid-containing feed stream must not comprise a racemic mixture of lactic acid. One of the two enantiomers should therefore be present in excess with respect to the other enantiomer. To obtain a chirally pure product it is preferable for the monomeric lactic acid present in the feed to have a chiral purity of at least 90%, more preferably at least 95% and in particular 99% or more. In the latter case this means that at least 99% of all the lactic acid (=100%) present in the feed stream will consist of (R)- or (S)-lactic acid.

The feed for the method according to the invention can be obtained in various ways. In the case of the synthetic preparation of lactic acid, suitable feeds can be obtained by the racemic product of the synthesis being subjected to an enantiomer separation, so that a product is obtained in which the one enantiomer is present in excess with respect to the other enantiomer, and which contains at least 80 wt % total acid and at least 80 wt % monomeric lactic acid. Enantiomer separation techniques are known.

In existing fermentation processes for preparing lactic acid, suitable feed streams for the method according to the invention can be obtained very effectively by means of a concentration step which at least comprises boiling down of a dilute lactic acid stream. In addition to, or instead of, boiling down, other concentration steps can also be employed, for example treatments in which use is made of membranes or molecular sieves. In principle, the feed can be any stream from the working-up stage after the fermentation, for example the product stream obtained from the purification step. Good results are obtained by a dilute, lactic-acid-containing stream, which contains 5–30 wt % lactic acid, being subjected to a concentration step.

The operation of concentrating the dilute, lactic-acid-containing stream can be carried out in any suitable manner. During the concentration step of lactic acid, the condition preferably applies that the temperature must not be too high, in order to prevent polymerization of lactic acid. The boiling-down operation is therefore preferably carried out at reduced pressure (from 100 to 500 mbar). The boiling-down can be carried out in one or more steps.

The dilute, lactic-acid-containing stream, in particular, is concentrated in a first concentration step in one or more falling-film evaporators and/or thin-film evaporators and/or lubricated-film evaporators, the pressure being from 100 to 500 mbar, in particular from 200 to 400 mbar. and the temperature being from 25° to 140° C., more preferably from 40° to 100° C. and in particular from 50° to 70° C. In said first concentration step, impurities having a boiling point lower than that of lactic acid, for example formic acid, are removed by evaporation. The bottom product obtained has a total acid content of at least 80 wt %, preferably at least 90 wt %, a monomer content of at least 80 wt %, preferably at least 90 wt %, and a chiral purity of at least 90%, preferably 95%, and in particular 99%.

Preferably, the product of the first concentration step is subjected to a second concentration step before distillation step (a) is carried out. The second concentration step is preferably carried out at a temperature of from 80° to 150° C., in particular at a temperature of from 100° to 140° C., and at a pressure from 50 to 250 mbar, in particular a pressure of from 60 to 150 mbar. The second concentration step is preferably carried out in such a way that the solution is brought into the vapour phase by means of film evaporation and the vapour is passed to a first distillation column. In the process, separation into two fractions takes place under reflux, the top product containing water, components which are more volatile than lactic acid, and at most 1 wt % lactic acid, preferably at most 0.1 wt % lactic acid, and the bottom product having a total acid content of at least 95 wt %, preferably at least 98 wt % lactic acid (based on the bottom product in total). The bottom product has a monomer content of at least 80 wt %, preferably at least 95 wt %, and a chiral purity of at least 90%, preferably at least 95% and in particular at least 98%. The film evaporation is preferably effected by means of lubricated-film evaporation, thin-film evaporation and/or falling-film evaporation, the distillation column or columns having a number of trays of from 1 to 10.

The distillation residue of distillation step (a) is recycled into the process upstream of crystallization step (b). The distillation residue is preferably subjected to a depolymerization step before said residue is recycled into the process, particularly because the residue contains oligomers or polymers of lactic acid, thereby allowing the yield of the process to be increased.

The depolymerization is preferably carried out by a mixture of from 30 to 70 wt %, preferably from 40 to 60 wt %, of an aqueous stream which preferably contains from 80 to 100 wt % water, and from 70 to 30 wt %, preferably from 60 to 40 wt %, of the residue of the second distillation step being heated for a period of from 1 to 10 hours under atmospheric pressure at a temperature of from 60° to 100° C.

Crystallization Step (b)

In principle, the known crystallization techniques can be employed. An example of such a technique is melt crystallization (cooling crystallization), which involves direct cooling of the condensed, liquid concentrate or distillate containing the (S)- or (R)-lactic acid in the molten state, so that the (S)- or (R)-lactic acid crystallizes out. It is preferable to keep the temperature at which crystallization occurs (the crystallization temperature) as low as possible, so that the formation of oligomers and polymers of lactic acid is limited as far as possible.

Melt crystallization is a process in which a crystalline material is obtained from a melt of the material to be crystallized. This technique is thoroughly described, for example, in Kirk-Othmer, Encyclopedia of Chemical Technology, Fourth Edition, Volume 7, pp. 723–727 (1993), in J. W. Mullin, "Crystallization", Third Revised Edition, Butterworth-Heinemann Ltd. pp. 309–323 (1993), and in J. Ullrich and B. Kallies, Current Topics in Crystal Growth Research, 1 (1994), which are incorporated herein as references. The greatest advantage of melt crystallization, compared with distillation, is that much less energy is required, as the enthalpy of fusion of organic compounds is generally lower than the enthalpy of evaporation. Furthermore, another advantage of melt crystallization compared with distillation is that the process generally can be carried out at much lower temperatures, which is advantageous if the organic compound is thermally unstable.

The melt crystallization can be carried out with the aid of a suspension crystallization or a layer crystallization, possibly in conjunction with a wash column or a centrifuge, or some other purification technique. Examples of suitable equipment and processes are described in Kirk-Othmer, Encyclopedia of Chemical Technology, Fourth Edition, Volume 7, pp. 723–727 (1993), in J. W. Mullin, "Crystallization", Third Revised Edition, Butterworth-Heinemann Ltd. pp. 309–323 (1993), and in J. Ullrich and B. Kallies, Current Topics in Crystal Growth Research, 1 (1994), whose contents are incorporated herein for reference.

It has also been found that crystallization of an aqueous solution gives very good results. With this crystallization treatment, the concentrated lactic acid solution is diluted with water and is then subjected to one or more cooling and/or evaporation crystallization steps. With these techniques, the concentrate or distillate is cooled directly (cooling crystallization) or concentrated by evaporation of the solvent, which is usually water (evaporation crystallization). The driving force for the crystallization in the case of the cooling crystallization technique is the bringing about of supersaturation in the concentrated lactic acid solution by lowering the temperature of the concentrated lactic acid solution. Owing to the lower temperature of the solution, the solubility decreases, and supersaturation may result. The driving force for the crystallization with the evaporation crystallization technique is the bringing about of supersaturation in the concentrated lactic acid solution by evaporation of solvent (increasing the concentration at constant temperature). This means that cooling or evaporation of solvent (usually water), respectively, results in effective removal of the heat of crystallization. During cooling or evaporation of water, crystallization of the lactic acid then occurs.

Another highly suitable crystallization technique is adiabatic crystallization, where the driving force for the crystallization is the bringing about of supersaturation in the concentrated lactic acid solution by heat neither being removed nor supplied. This involves lowering the temperature of the concentrated solution (solvent evaporates) and increasing the concentration of lactic acid (two effects: (a) solvent evaporates and (b) the temperature of the concentrated lactic acid solution drops, as a result of which the solubility decreases and supersaturation may result).

According to the invention, the crystallization step (b) is preferably carried out by adiabatic crystallization or cooling crystallization, in particular by means of adiabatic crystallization. Preferably, the crystallization involves the addition of seed crystals to the concentrated lactic acid solution.

The lactic acid which has crystallized out can then be separated from the remaining liquid, or (mother liquor) in the in the known ways of solid-liquid separation.

Examples of suitable separation techniques for separating the lactic acid crystals from the mother liquor are centrifuging, decanting, filtration, separation with the aid of one or more wash columns, or a combination of two or more of these techniques. Within the scope of the invention it was found that centrifuging is particularly expedient.

The mother liquor obtained still always contains considerable quantities of lactic acid. For optimal process control it is therefore preferable to recycle said mother liquor into the production process.

The lactic acid crystals obtained, having been isolated, are immediately dissolved in a suitable solvent, generally water, to prevent the hygroscopic lactic acid crystals from caking together. The concentration of the lactic acid solution thus obtained can, in principle, have any desired value. In practice, this will generally vary from 30 to 95 wt %. Concentrations often encountered commercially are 80–90 wt %.

According to the invention, that embodiment of the method which is particularly preferred is (1) at least one concentration step of the feed to produce a concentrated lactic acid solution, (2) a distillation step at reduced pressure of the concentrated lactic acid solution in a short-path distillation apparatus and (3) adiabatic crystallization of the product obtained in the distillation.

The invention will now be illustrated by way of the following examples.

EXAMPLE 1

A lactic acid solution in water (67.8 wt % of lactic acid) was concentrated, with the aid of thin-film distillation at 0.1 bar and 120° C. and with a flow of 10 ml/min, to produce a concentrate which contained 97.1 wt % lactic acid. This concentrate was then distilled using a short-path distillation apparatus (UIC, KDL-4) at a pressure of 1 mbar and a temperature of 130° C. with a flow of 15 ml/min. The product obtained was virtually colourless. A quantity of 319 g of the distillate obtained was then diluted with 15 ml of water and, over a period of 6 hours, cooled from 38.5° C. to 28.5° C. The crystal slurry obtained in the process was separated from the crystals and mother liquor with the aid of a laboratory centrifuge.

The yield was 143 g (45%). The crystals were dissolved in a small amount of water for further analyses (see Table 1).

TABLE 1

|  | Total acid[a] (%) | Free acid[b] (%) | Colour (APHA) | Colour after heat test (APHA) | Chiral parity (%)[c] | Total N (ppm)[d] | Total sugars (ppm)[e] |
|---|---|---|---|---|---|---|---|
| Lactic acid before concentrating | 67.8 | 66.5 | 2300 | — | 97.1 | 710 | 4900 |
| Lactic acid after concentrating | 97.1 | 95.1 | 2770 | — | 97.0 | 1150 | 7300 |
| Lactic acid after distillation | 99.6 | — | 83 | 250 | 97.1 | <5 | <100 |
| Lactic acid after crystallization and dissolving in water | 91.8 | — | <5 | <5 | 99.93 | <5 | <100 |

[a]Total acid: acid content after saponification of intermolecular ester bonds with base (wt % lactic acid).
[b]Free acid: direct acid group titration (wt % lactic acid).
[c]The chiral purity was determined with the aid of GLC.
[d]Reduction with hydrogen, followed by coulometric titration of the ammonia formed.
[e]Hydrolysis with sulphuric acid, followed by photometric determination using neocuproine.

EXAMPLE 2

A crystallizer equipped with a 60 l stirred vessel and a NESLAB RTE111 thermostat bath was charged with 27.5 kg of freshly distilled (R)-lactic acid (see Example 1). The lactic acid was diluted with 0.76 kg of water, to lower the crystallization temperature. The seeding temperature of the dilute lactic acid was determined and found to be 39.5° C. A seed crystal slurry was prepared by a mixture of 60 g of crystals of (R)-lactic acid and 5 g of deionized water being blended for 15 minutes at maximum speed in a laboratory ball mill (Retsch S1).

The mixture in the crytallizer was cooled to 39.3° C., and 35 g of the seed crystal slurry were added. The seed crystals were allowed to grow without cooling for a period of 30 minutes. During this period the temperature rose to 39.4° C. A linear cooling program was started after 30 minutes: from 39.5° C. to 25° C. over 16 hours. At a temperature of 26.0° C. the cooling program was stopped, as the viscosity of the slurry became too high. The slurry was stirred for a further 6 hours, and was then centrifuged (Merck: Ferrum, 10 minutes, speed: 550). The resulting lactic acid crystals (13.3 kg, yield 48%, based on lactic acid) and most of the mother liquor (13.5 kg) were collected; a small fraction of the mother liquor remained behind in the centrifuge. A small portion of the crystals obtained was diluted to 90% and dissolved with heating. The results of the analyses are shown in Table 2.

TABLE 2

|  | Colour (APHA) | Colour after heat test (APHA) | Chiral purity (%) | Total acid (wt %) | Total N (ppm) |
|---|---|---|---|---|---|
| Feed | 240 | 810 | 95.4 | 97.0 | 80 |
| Mother liquor | 310 | — | 91.0 | — | — |
| Product (as 90%) | 13 | 20 | 99.76 | — | <5 |

The conclusion from this experiment is that without optimal chiral purity of the feed it is possible to obtain crystalline lactic acid having a chiral purity of more than 99.5%. The yield, based on lactic acid, is 48%. Recycling the mother liquor easily allows this to be raised to about 60%.

EXAMPLE 3

This example describes gustatory and olfactory tests of the product according to the invention. The comparative tests were carried out as triangular tests. The descriptive tests were carried out by means of scoring in terms of established descriptors.

Odour

The descriptive tests of the lactic acid samples were carried out in a number of steps. In the first instance, using a group of 20 persons, a list of descriptors was compiled which allowed the separate samples to be described. This was followed by a brief training session, in which these persons were trained for odour recognition of the descriptors. Finally, the separate samples were scored in terms of various descriptors, use being made of a hedonistic scale of 1–7 (a widely used scale in descriptive analysis). With the aid of scoring lists, a final assessment of the lactic acid samples was drawn up. This assessment is a representation of trends with respect to odour of the samples. The results are shown in Table 3 (1: very faint; 7: very strong; the reference products are commercially available).

TABLE 3

|  | Lactic acid (according to the invention) | Lactic acid (reference 1) | Lactic acid (reference 2) |
|---|---|---|---|
| Mildly acid | 4 | n.p.[a] | n.p. |
| Strongly acid | n.p. | 2 | 2 |
| Sweet | n.p. | n.p. | 3 |
| Alcohol/ester | 2 | n.p. | 6 |
| Burnt | n.p. | n.p. | 5 |
| Ethyl lactate | n.p. | n.p. | n.p. |
| Sulphurous | n.p. | 5 | n.p. |
| Musty | n.p. | 6 | 6 |
| Greasy | n.p. | 7 | n.p. |

[a]n.p. not present (value 0)

Taste

TABLE 4

| Lactic acid (according to the invention) | Fresh, mildly acidic, no odd taste |
|---|---|
| Lactic acid (reference 1) | Has an odd taste (peanuts, greasy), no acidic taste as with lactic acid according to the invention |
| Lactic acid (reference 2) | Good taste. No odd taste. Sharper acidic |

TABLE 4-continued taste than lactic acid according to the invention

These tests show that the lactic acid according to the invention, compared with the reference acids, has a pleasant, mildly acid odour. The odour is mildly acid in character with an alcohol/ester subsidiary odour component. The lactic acid according to the invention is of high purity. The taste is freshly acidic. There is no odd taste. Lactic acid (reference 1) has a sharp odour (greasy, sulphurous, musty) and has a very unpleasant odd taste and after taste (greasy). Lactic acid (reference 2) contains many odour components and a strong bouquet and is not pure. The taste of lactic acid (reference 2) is good, but is sharper than that of the lactic acid according to the invention.

What is claimed is:

1. Method of industrial-scale purification of lactic acid, the method comprising the steps of:
   (a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1, and
   (b) subjecting the concentrated lactic acid solution to a crystallization to form a pure lactic acid.

2. Method of industrial-scale purification of lactic acid, the method comprising the steps of: p1 (a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1, and
   (b) subjecting the concentrated lactic acid solution to a crystallization to form a pure lactic acid,
wherein in step (b) as solvent only water is used.

3. Method of industrial-scale purification of lactic acid, the method comprising the steps of:
   (a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1, and
   (b) subjecting the concentrated lactic acid solution to a crystallization to form a pure lactic acid,
wherein in step (b) seed crystals are added to the concentrated lactic acid solution.

4. Method of industrial-scale purification of lactic acid, the method comprising the steps of:
   (a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1, and
   (b) subjecting the concentrated lactic acid solution to a crystallization to form a pure lactic acid,
wherein the reduced-pressure distillation is carried out at a pressure of from 0.1 to 20 mbar and a temperature of from 100° to 200° C.

5. Method according to claim 4, wherein the reduced-pressure distillation is carried out at a pressure of from 0.2 to 10 mbar and a temperature of from 110° to 140° C.

6. Method according to claim 1, wherein the residue of the distillation is recycled into the process upstream of crystallization step (b).

7. Method according claim 1, wherein the concentrated lactic acid solution, prior to distillation step (a), is passed over a column containing activated carbon.

8. Method according to claim 1, wherein the concentrated lactic acid solution, prior to distillation step (a), is passed over an ion exchanger.

9. Method according to claim 1, wherein the concentrated lactic acid solution, prior to distillation step (a), is passed over a column containing activated carbon and then over an ion exchanger.

10. Method according to claim 1, wherein the crystallization step (b) is carried out in one or more cooling crystallizers, evaporation crystallizers and/or adiabatic crystallizers.

11. Method of industrial-scale purification of lactic acid, the method comprising the steps of:
    (a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1, and
    (b) subjecting the concentrated lactic acid solution to a crystallization to form a pure lactic acid,
wherein the crystallization step (b) is carried out in an adiabatic crystallizer.

12. Method according to claim 1, wherein the product stream of the crystallization step (b) is separated, by means of a solid-liquid separation, preferably centrifuging, into a mother liquor and lactic acid crystals.

13. Method according to claim 1, wherein the concentrated lactic acid solution is obtained from lactic acid prepared by fermentation.

14. Method of industrial-scale purification of lactic acid, the method comprising the steps of:
    (a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1, to form a lactic acid concentrate, wherein the concentrated lactic acid solution is obtained from a dilute lactic acid stream produced by fermentation, and
    (b) subjecting the lactic acid concentrate to a crystallization to form a pure lactic acid, wherein the crystallization is carried out by:
       (i) direct cooling of the lactic acid concentrate in one or more melt crystallizers, and/or
       (ii) diluting the lactic acid concentrate with water and effecting crystallization in one or more cooling crystallizers and/or evaporation crystallizers, and/or
       (iii) effecting crystallization in one or more adiabatic crystallizers.

15. Method according to claim 14, wherein the reduced-pressure distillation of the concentrated lactic acid solution is carried out:
    (i) with a short-path distillation apparatus, or
    (ii) by bringing the concentrated lactic acid solution in the vapour phase by film evaporation and passing the vapour phase to a distillation column.

16. Method according to claim 14, wherein the reduced-pressure distillation is carried out at a pressure of from 0.1 to 20 mbar and a temperature of from 100° to 200° C.

17. Method according to claim 14, wherein the residue of the distillation is recycled into the process upstream of crystallization step (b).

18. Method according to claim 14, wherein in step (b) seed crystals are added to the lactic acid concentrate.

19. Method according to claim 14, wherein step (b) is carried out by cooling crystallization or adiabatic crystallization.

20. Method of industrial-scale purification of lactic acid, the method comprising the steps of:
   (a) reduced-pressure distillation of a concentrated lactic acid solution having a total acid content of at least 95 wt % and a content of monomeric lactic acid of at least 80 wt %, based on the concentrated lactic acid solution, the ratio between the lactic acid enantiomers in the concentrated lactic acid solution not being equal to 1 to form a lactic acid concentrate, wherein the concentrated lactic acid solution is obtained from a dilute lactic acid stream produced by fermentation, and
   (b) subjecting the lactic acid concentrate to a crystallization to form a pure lactic acid, wherein the crystallization is carried out by:
      (i) direct cooling of the lactic acid concentrate in one or more melt crystallizers, and/or
      (ii) diluting the lactic acid concentrate with water and effecting crystallization in one or more cooling crystallizers and/or evaporation crystallizers, and/or
      (iii) effecting crystallization in one or more adiabatic crystallizers,
   wherein step (b) is carried out by adiabatic crystallization.

21. Method according to claim 14, wherein the product stream of the crystallization step (b) is separated, by means of a solid-liquid separation, into a mother liquor and lactic acid crystals.

22. Method according to claim 21, wherein the solid-liquid separation is centrifuging.

23. Method according to claim 21, wherein the solid-liquid separation is performed with the aid of a wash column.

* * * * *